United States Patent [19]

Lohse et al.

[11] 3,976,676

[45] Aug. 24, 1976

[54] POLYSILOXANE COMPOUNDS CONTAINING HYDROXYL GROUPS

[75] Inventors: Friedrich Lohse, Oberwil; Heinz Rembold, Arlesheim; Dieter Baumann, Birsfelden, all of Switzerland; Kurt Munk, Wyhlen, Germany

[73] Assignee: Ciba-Geigy Corporation, Ardsley, N.Y.

[22] Filed: Mar. 17, 1975

[21] Appl. No.: 558,987

[30] Foreign Application Priority Data

Mar. 25, 1974  Switzerland.......................... 4106/74

[52] U.S. Cl............................................ 260/448.8 R
[51] Int. Cl.$^2$............................................ C07F 7/18
[58] Field of Search .............................. 260/448.8 R

[56] References Cited
UNITED STATES PATENTS

| | | |
|---|---|---|
| 3,293,211 | 12/1966 | Krimm et al............. 260/448.8 R X |
| 3,317,460 | 5/1967 | Clark et al. ............... 260/448.8 R X |
| 3,576,028 | 4/1971 | Fish............................... 260/448.8 R |
| 3,600,418 | 8/1971 | Bailey et al. .................. 260/448.8 R |

FOREIGN PATENTS OR APPLICATIONS 341,816   6/1972   U.S.S.R......................... 260/448.8 R

*Primary Examiner*—Paul F. Shaver
*Attorney, Agent, or Firm*—Luther A. R. Hall

[57] ABSTRACT

Polysiloxanes containing hydroxyl groups are manufactured by reacting polysiloxanes containing alkoxy groups with aliphatic or cycloaliphatic-alipatic diols in the presence of a catalyst at elevated temperatures. The new polysiloxanols can be used as modifiers for organic resins, such as urethane resins or epoxide resins, and give flexible hydrophobic plastics having valuable mechanical properties.

4 Claims, No Drawings

POLYSILOXANE COMPOUNDS CONTAINING HYDROXYL GROUPS

The present invention relates to new polysiloxane compounds containing hydroxyl groups, processes for their manufacture and the use of the new polysiloxanols for the manufacture and modification of organic resins.

Plastics modified with siloxane compounds are known. Polysiloxanes with hydroxyl end groups have also already been proposed for the purpose of modifying synthetic resins. British Patent Specification No. 880,022 describes a process for the manufacture of polyoxyalkylene-polysiloxanediol block copolymers by reaction of polyoxyalkylene glycols of a particular chain length with polysiloxanes with two alkoxy end groups. Where these polysiloxanediol block copolymers are water-insoluble compounds, they are used as plasticisers for rubbers. However, when used as modifiers for synthetic resins they suffer from the disadvantage that they do not impart hydrophobic properties to the modified resin.

German Auslegeschrift 1,618,836 proposes trisiloxanols, of which the hydroxyl groups are bonded directly to the Si atoms, as modifiers for organic resins, such as polyester, urethane and epoxide resins. However, these siloxanols suffer from the disadvantage that their processing with organic resins presents difficulties so that they are not very suitable for use as modifiers. Furthermore, the siloxanols cannot be incorporated into the lattice structure without elimination of low molecular condensates so that heterogeneous moulded materials pervaded by gas bubbles are obtained, which furthermore exhibit less good mechanical properties.

It has now been found that reaction of polysiloxanes containing hydroxyl, alkoxy or acyloxy groups with certain glycols gives new polysiloxanols which do not suffer from the abovementioned disadvantages, can easily be manufactured in accordance with the invention and impart advantageous properties to the modified resin, in particular in respect of very low water absorption.

Accordingly, the subject of the present invention are new polysiloxane compounds containing hydroxyl groups, of the formula I

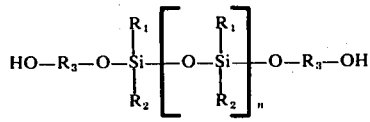

wherein $R_1$ and $R_2$ are identical or different and each denote a methyl, ethyl, propyl or phenyl group, the —O—$R_3$—OH group or the

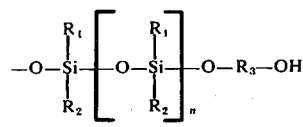

group, wherein $R_1$ and/or $R_2$ can denote different substituents within the polysiloxane chain, $R_3$ denotes an alkylene radical with 2–8 C atoms, an alkyl-substituted alkylene radical with 2–8 C atoms in the alkylene chain, which chain can optionally be interrupted by a

radical, or a cycloaliphatic-aliphatic, heterocyclic-aliphatic or aromatic-aliphatic radical and $n$, or the sum of $n$, denotes a number from 1 to 30.

Preferably, the polysiloxanes of the formula I contain 2 – 4 hydroxyl groups, and $n$ or the sum of $n$ denotes a number from 2 to 20.

In particular, in the formula I, $R_1$ and $R_2$ each denote a methyl, ethyl, propyl or phenyl group, and $R_1$ and $R_2$ on the same Si atom denote identical substituents and within the siloxane chain denote different substituents, $R_3$ denotes an alkylene radical with 2 – 6 C atoms, an alkylene radical, substituted by lower alkyl groups, with 2 – 6 C atoms in the alkylene chain, or a cycloaliphatic-aliphatic radical, and $n$ denotes a number from 2 to 20.

Particularly interesting compounds of the formula I are those wherein, in the linear polysiloxane chain, dimethyl siloxane units alternate with dipropylsiloxane or diphenylsiloxane units and $R_3$ denotes a lower alkyl-substituted alkylene radical, with 2 or 3 C atoms, preferably 3 C atoms, in the alkylene chain, obtained by removing the primary and secondary hydroxyl group.

The new polysiloxane compounds containing hydroxyl groups, of the formula I, are obtained by reacting 1 mol of a polysiloxane of the formula II

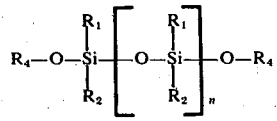

wherein the radicals $R_4$ each denote a hydrogen atom, an alkyl group or an acyl group, with 2 mols of a glycol of the formula III

         III.

at elevated temperatures and, if appropriate, in the presence of a catalyst, to give compounds of the formula I.

It is preferred to start from those compounds of the formula II wherein $R_1$ and $R_2$ each denote a methyl, ethyl, propyl or phenyl group, and $R_1$ and $R_2$ on the same Si atom denote identical substituents and within the siloxane chain denote different substituents, $R_4$ denotes a lower alkyl or acyl group, preferably a lower alkyl group with 1 – 3 C atoms, and $n$ denotes a number from 2 to 20, and to react these with compounds of the formula III, wherein $R_3$ denotes an alkylene radical with 2 – 6 C atoms, an alkylene radical, substituted by lower alkyl groups, with 2 – 6 C atoms in the alkylene chain or a cycloaliphatic-aliphatic radical.

In a particular embodiment, the polysiloxanes used are compounds of the formula II wherein, in the linear polysiloxane chain, dimethylsiloxane units alternate with dipropylsiloxane or diphenylsiloxane units, and $R_4$ denotes the methyl, ethyl or propyl group, and are reacted with glycols of the formula III, wherein $R_3$ denotes an alkylene radical, substituted by lower alkyl groups, with 2 or 3 C atoms, preferably 3 C atoms, in the alkylene chain and containing a primary and a secondary hydroxyl group in the molecule.

The reaction of the polysiloxanes of the formula II, containing hydroxyl, alkoxy or acyloxy groups, with the glycols of the formula III is carried out in accordance with known processes. For this purpose, the two components are mixed hot, in approximately stoichiometric amounts, and are reacted in the temperature range of about 100° to 250°C, preferably 150° to 220°C, until the theoretical amount of water, alcohol or monocarboxylic acid liberated in the reaction is obtained. If the glycols of the formula III which are used are glycols with two primary or two secondary hydroxyl groups, these glycols are advantageously employed in a stoichiometric excess, and the excess is distilled off continuously during the reaction. The end of the reaction can also be determined with the aid of a sample which has been cooled to room temperature. When the reaction has been completed, phase separation no longer occurs in a cooled sample.

As a rule, the presence of a catalyst is superfluous in this process. However, basic, acid or neutral catalysts can be used to accelerate the reaction. The catalysts used are preferably organic titanium compounds, such as tetrabutyl titanate or tetraisopropyl titanate, quaternary ammonium salts, such as tetramethylammonium chloride, aluminium halides and boron halides or carboxylic acids, especially trifluoroacetic acid, as well as the catalysts named in the initially mentioned British Patent Specification 880,022.

The polysiloxanes, containing reactive groups, of the formula II, are known compounds. The polysiloxanes, containing hydroxyl groups, of the formula II can be manufactured, for example, in accordance with the process described in French Patent 950,582, by hydrolysing dialkyldichlorosilanes and/or diphenyldichlorosilanes in sulphuric acid. A summarising description of further processes for the manufacture of the polysiloxanes of the formula II is given by W. Noll in "Chemie und Technologie der Silicone" ("Chemistry and Technology of the Silicones"), Verlag Chemie GmbH, 1968, on pages 162–206.

Examples which may be mentioned of polysiloxanes of the formula II containing alkoxy or acyloxy groups are methoxy-, ethoxy- and acetoxy-terminated polydimethylsiloxanes, polymethylpropylsiloxanes, polymethylphenylsiloxanes and polyphenylsiloxanes. The average molecular weight of these polysiloxanes lies in the range of 300 to 3,000, preferably 500 to 2,500.

The glycols of the formula III are also known compounds and the following may be mentioned as preferred glycols containing a primary and a secondary hydroxyl group: propane-1,2-diol, butane-1,3-diol, 2,2-dimethylhexane-1,3-diol, 2,2,4-trimethyl-pentane-1,3-diol and 2-ethyl-hexane-1,3-diol.

The following may be mentioned as primary or secondary glycols of the formula III: ethylene glycol, propane-1,3-diol, neopentylglycol, butane-1,4-diol, hexane-1,6-diol, 2,2-diethylpropane-1,3-diol, 2-methyl-2-propyl-propane-1,3-diol, 2,2,4- or 2,4,4-trimethyl-hexane-1,6-diol, 2-methyl-2-ethylpropane-1,3-diol, octane-1,8-diol, hydroxypivalic acid neopentylglycol ester, 1,1-, 1,2-, 1,3- and 1,4-bis-(hydroxymethyl)-cyclohexane and the corresponding unsaturated cyclohexene derivatives, such as 1,1-bis-(hydroxymethyl)-cyclohexene, 1,4-bis-(hydroxymethyl)-cyclohexane and 1,4-bis-(hydroxymethyl)-benzene, bis-oxyalkylated bisphenol A, bis-oxyalkylated hydroquinone, 2,2-bis-(4-hydroxycyclohexyl)-propane and the diols of the heterocyclic-aliphatic series which are obtained by addition reaction of 2 mols of an alkene oxide, such as ethylene oxide, propene oxide, 1,2-butene oxide or styrene oxide with 1 mol of a mononuclear or polynuclear N-heterocyclic compound, such as hydantoin and its derivatives, dihydrouracil and its derivatives, barbituric acid and its derivatives, benzimidazolone and tetrahydrobenzimidazolone and their derivatives, bishydantoins and bis-dihydrouracils and their derivatives. The following may be mentioned as examples: 1,3-di-($\beta$-hydroxyethyl)-5,5-dimethylhydantoin, 1,3-di-($\beta$-hydroxy-n-propyl)-5,5-dimethylhydantoin, 1,3-di-($\beta$-hydroxy-n-propyl)-5-isopropylhydantoin, 1,3-di-($\beta$-hydroxy-n-propyl)-5-ethyl-5-methylhydantoin, 1,3-di-($\beta$-hydroxyethyl)-benzimidazolone, 1,3-di-($\beta$-hydroxyethyl)-tetrahydrobenzimidazolone, 1,1'-methylene-bis-(3-$\beta$-hydroxyethyl-5,5-dimethylhydantoin), 1,1'-methylene-bis-(3-$\beta$-hydroxy-n-propyl-5,5-dimethylhydantoin) and 1,1'-methylene-bis-(3-$\beta$-hydroxypropyl-5-isopropylhydantoin).

Polysiloxane diols of the formula I can also be obtained by reacting 1 mol of a polysiloxane of the formula IV

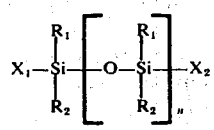

IV.

wherein $X_1$ and $X_2$ each denote a hydrogen atom or chlorine atom, with 2 mols of a glycol of the formula III, at elevated temperatures, with elimination of hydrogen or hydrogen chloride.

The reaction conditions in this process in general correspond to those in the process previously described. If a polysiloxane of the formula IV which contains chlorine is used, the reaction is preferably carried out in the presence of a hydrogen chloride acceptor, such as pyridine, in order to remove the hydrogen chloride produced.

The compounds of the formula IV are also known compounds, the manufacture of which is described by W. Noll in "Chemie und Technologie der Silicone" ("Chemistry and Technology of the Silicones") (Verlag Chemie GmbH; 1968) on page 166.

The polysiloxanols according to the invention can be used for the manufacture and modification of organic resins, such as urethane or epoxide resins and give flexible, hydrophobic plastics having valuable mechanical properties. The polysiloxanols according to the invention are colourless to slightly coloured liquids and, compared to conventional polysiloxanes, have better compatibility with curable mixtures consisting of polyepoxides and polycarboxylic acid anhydrides, that is to say are more easily processable with these. The new polysiloxanols are also valuable agents for imparting hydrophobic properties to epoxide resins plasticised with polyesters. It is known that plasticised epoxide resins frequently suffer from the disadvantage that with increasing plasticisation the moulded materials manufactured from these resins tend to show increased water absorption. As can be seen from the Use Example, the water absorption of the moulded materials manufactured from plasticised epoxide resins modified with polysiloxanediols is extremely low even after several hours in boiling water.

The polysiloxanols according to the invention can be processed together with curable mixtures, consisting of epoxide resins and polycarboxylic acids or polycarboxylic acid anhydrides, in accordance with all known processes. If desired, the curing can also be carried out in two steps by first prematurely discontinuing the curing reaction, which gives a curable precondensate which is still fusible and soluble (a so-called "B-stage"). It is also possible to modify epoxide resins by reacting the polysiloxanol according to the invention with a polycarboxylic acid or a polycarboxylic acid anhydride to give a pre-adduct containing carboxyl groups and then to use this for curing epoxide resins or for the manufacture of curable adducts containing epoxide groups. All polyepoxides, polycarboxylic acids and polycarboxylic acid anhydrides are suitable for this purpose. Both in the manufacture of the pre-adduct containing carboxyl groups and in the manufacture of the adduct containing epoxide groups the carboxylic acid component or epoxide resin component is preferably employed in an equivalent excess. This means that per 1 hydroxyl equivalent of the polysiloxanol at least 2 carboxyl equivalents, but preferably more than 2 carboxyl equivalents, of the carboxylic acid are employed.

EXAMPLE 1

764 g (5.2 mols) of 2-ethylhexane-1,3-diol are added to 2,350 g (2.6 mols) of a linear poly-methyl-phenyl-siloxane containing methoxy end groups and having an average molecular weight of 900, in a sulphonation flask equipped with a stirrer, thermometer and descending condenser; a turbid reaction mixture results. On heating to about 90°C, the mixture becomes homogeneous. It is then heated to 180° – 190°C, whereupon the elimination of methanol starts. After about 3 hours, 170 g of distillate have been obtained; it was also possible to identify this distillate as methanol by gas chromatography. It still contains further smaller amounts of low-boiling siloxane derivatives; the reaction mixture is then freed from further low-boiling siloxane derivatives by treating it for 1 hour at 180°C under a low vacuum (about 80 – 100 mm Hg). This gives a further 45 g of distillate. The resulting product is a colourless liquid having a hydroxyl equivalent weight of 606. Elementary analysis, and the nuclear magnetic resonance spectrum, confirm that the product obtained consists of polymethylphenylsiloxanediol.

EXAMPLE 2

48.0 g (0.2 mol) of 2,2-bis(4'-hydroxycyclohexyl)-propane and 300 mg of tetraisopropyl titanate, as the catalyst, are added to 90 g (0.1 mol) of a linear poly-methyl-phenyl-siloxane containing methoxy end groups and having an average molecular weight of 900, in the same apparatus as described in Example 1; a 2-phase reaction mixture results. On warming to about 135° – 138°C, the mixture becomes homogeneous and at 170°C a slow elimination of methanol starts. After 5 hours at 170°C and a further 5 hours at 200°C, 6 ml of distillate are obtained, and the elimination of methanol is complete. A further 2 g of distillate are obtained by applying a vacuum of 80 – 100 mm Hg. The resulting product is a light yellow liquid having a hydroxyl equivalent weight of 705.

EXAMPLE 3

115.1 g (0.75 mol + 5% excess) of 2,2-dimethylhexane-1,3-diol are added to 240 g (0.25 mol) of a poly-methyl-phenyl-siloxane, containing three methoxy groups and having an average molecular weight of 960, in the same apparatus as described in Example 1; a two-phase reaction mixture results. This becomes homogeneous on warming to 60° – 70°C. To carry out the condensation reaction, the mixture is heated for 10 hours under nitrogen at 180° – 190°C, in the course of which methanol distils off. The reaction mixture is then allowed to continue reacting for 3 hours under 15 mm Hg in order to complete the reaction and remove all low-boiling constituents. This also results in any unconverted 2,2-dimethylhexane-1,3-diol being distilled off, as can also be established by gas chromatography. The resulting reaction product is a colourless, clear oil of low viscosity, having a hydroxyl equivalent weight of 2,103. In the H-NMR spectrum (100 Mc; CDCl$_3$), the signals of the SiOCH$_3$ protons at $\delta$ 3,4 – 3.6 have disappeared and been replaced by the Si-O-CH$_2$ proton signals at $\delta$ 3.7 – 3.8.

EXAMPLE 4

481.8 g (3 mols + 10% excess) of 2-ethylhexane-1,3-diol were added to 1,635 g (1.5 mols) of a linear poly-methyl-phenylsiloxane containing methoxy end groups and having an average molecular weight of 1,090, in the apparatus according to Example 1, and the mixture was heated to 180° – 190°C under nitrogen for 7 hours, during which 108 g of distillate are obtained; gas chromatography showed the distillate to contain 90% of methanol. In addition, some higher-boiling components are present. The reaction mixture is then allowed to continue to react for a further 2 hours at 170°C/15 mm Hg in order to separate all lower-boiling components from the reaction product. This gives a further 143.0 g of distillate. The resulting reaction product is a colourless liquid having a hydroxyl equivalent of 1,170.

USE EXAMPLES

EXAMPLE I 50 parts by weight of the glycol containing polysiloxane groups, manufactured according to Example 1, are mixed with 100 parts by weight of an adduct containing epoxide groups, the manufacture of which is described below, 15 parts by weight of hexahydrophthalic anhydride and 35 parts by weight of an acid adduct curing agent, the manufacture of which is also described below, and 1 part by weight of a solution of 0.82 part by weight of sodium in 100 parts by weight of 2,4-dihydroxy-3-hydroxymethylpentane as the catalyst, at 120°C, and the mixture is poured into an aluminium mould warmed to 120°C and is cured at this temperature for 6 hours.

The castings obtained have the following properties: Water absorption after 100 hours at 100°C: 0.4%; after 180 hours at 100°C: 1.5%.

Manufacture of the Adduct Containing Epoxide Groups 3,300 g of an acid polyester, obtained from 11 mols of sebacic acid and 10 mols of hexanediol and having an acid equivalent weight of 1,530, are allowed to react with 794 g of 3-(3',4'-epoxycyclohexyl)-8,9-epoxy-2,4-dioxaspiro(5.5) undecane having an epoxide content of 6.8 equivalents/kg (corresponding to a ratio of 1 carboxyl group of the polyester: 2.5 equivalents of epoxide groups) for 3 hours at 140°C under a nitrogen atmosphere.

Manufacture of the Acid Adduct Curing Agent 30 g of hexahydrophthalic anhydride, 50 g of an oligomeric fatty acid mixture manufactured by dimerisation of unsaturated higher fatty acids and having an acid equivalent weight of 292 and 7.5 g of 1,4-butanediol diglycidyl ether are reacted for 6 hours at 140°C. 30 g of dodecenylsuccinic anhydride are added to 70 g of the adduct obtained.

COMPARISON EXAMPLE

Instead of 50 parts by weight of the glycol containing polysiloxane groups, 40 parts by weight of a polyester containing hydroxyl end groups and manufactured by reaction of 7 mols of adipic acid, 4 mols of neopentylglycol and 4 mols of butane-1,4-diol at 165°C (until the hydroxyl equivalent weight is between 800 and 1,000) are mixed with 100 parts by weight of the adduct containing epoxide groups, described above, 15 parts by weight of hexahydrophthalic anhydride, 35 parts by weight of the acid adduct curing agent described above and 1 part by weight of the same catalyst, and the mixture is cured under the same conditions.

The resulting castings have the following properties: Water absorption after 100 hours at 100°C: > 10%; after 120 hours at 100°C: samples destroyed.

EXAMPLE II 90 parts by weight of the triol, containing polysiloxane groups, manufactured according to Example 3 are mixed with 100 parts by weight of 3′,4′-epoxycyclohexylmethyl-3,4-epoxycyclohexylcarboxylate, having an epoxide content of 7.3 equivalents/kg, 46 parts by weight of hexahydrophthalic anhydride, 1.5 parts by weight of butanediol diglycidyl ether, 7.5 parts by weight of dodecenylsuccinic anhydride, 108.6 parts by weight of an oligomeric fatty acid mixture obtained by dimerisation of unsaturated higher fatty acids and having an acid equivalent weight of 292 and 1 part by weight of a solution of 0.82 part by weight of sodium in 100 parts by weight of 2,4-di-hydroxy-3-hydroxy-methylpentane as the catalyst, as well as with 400 parts by weight of quartz powder (K 8) as the filler, at 120°C, and the mixture is poured into an aluminium mould, warmed to 120°C and is cured for 10 hours at this temperature. The castings obtained have the following properties: Water absorption after 100 hours at 100°C: 0.25%; Water absorption after 200 hours at 100°C: 0.40%.

EXAMPLE III a. Manufacture of an adduct, containing carboxyl groups, from polysiloxane glycol and dimerised fatty acid.

620 g (0.53 hydroxyl equivalent) of the polysiloxane glycol manufactured in Example 4 and 650 g (2.2 carboxyl equivalents) of dimerised fatty acid (tradename "Empol 1024") are heated to 160°C in a stream of $N_2$ in a 1.5 l sulphonation flask. The water produced in forming the ester is removed in the stream of $N_2$. The mixture is kept at 160°C for 20 hours, until the carboxyl equivalent weight is about 1,400. The product is a yellow clear ester which becomes turbid on standing or on cooling to below 30°C.

Viscosity at 25°C: 6,500 – 8,000 cP.

Yield: 97% of theory.

b. Manufacture of an adduct containing epoxide groups 338 g (1.1 carboxyl equivalents) of the ester obtained above are mixed with 151 g (4.7 epoxide equivalents) of 3′,4′-epoxycyclohexylmethyl-3,4-epoxycyclohexylcarboxylate having an epoxide content of 7.17 equivalents/kg and the mixture is heated to 100°C in a sulphonation flask. After 4–5 hours reaction at this temperature, the epoxide content is 4.2–4.3 equivalents/kg (theory, 4.19). The reaction is then discontinued by allowing the reaction product to cool to room temperature. The product is a clear resin of a medium brown colour.

Viscosity at 25°C: 10,000 – 12,000 cP.

Yield: 98% of theory.

c. Manufacture of mouldings 1. 151 g of the acid ester, containing polysiloxane groups, which has been manufactured according to Example IIIa) are mixed with 72 g of 3′,4′-epoxycyclohexylmethyl-3,4-epoxycyclohexylcarboxylate having an epoxide content of 7.17 equivalents/kg, 46 g of hexahydrophthalic anhydride, 1.5 g of butanediol diglycidyl ether, 7.5 g of dodecenylsuccinic anhydride, 6 g of an oligomeric fatty acid mixture obtained by dimerisation of unsaturated higher fatty acids and having an acid equivalent weight of 292 and 1 g of a solution of 0.82 g of sodium in 100 g of 2,4-di-hydroxy-3-hydroxy-methylpentane as the catalyst, with the addition of 400 g of quartz powder as the filler, at 120°C, and the mixture is poured into an aluminium mould warmed to 120°C and is cured at this temperature for 10 hours.

The castings obtained have the following properties: $H_2O$ absorption

| | | |
|---|---|---|
| at 23°C after | 20 days | 0.5% |
| at 23°C after | 100 days | 0.9% |
| at 100°C after | 200 hours | 2.0% |
| at 100°C after | 1,000 hours | 6.1% |
| Resistance to boiling water | | 1,500–1,700 hours |
| Dielectric loss factor (tg δ) at 120°C | | 11% |
| Tracking resistance (DIN 53,480) | | >3,000 drops |
| Surface resistance (DIN 53,482) | | $6 \times 10^{14} \Omega$ |
| $H_2O$ vapour permeability by the Deeg and Frosch method at 23°C | | $2.8 \times 10^{-8}$ |
| Arcing resistance (ASTM 495) | | level 3 |

2. 223 g of the epoxide resin, containing polysiloxane groups manufactured according to Example IIIb) are mixed with 46 g of hexahydrophthalic anhydride, 1.5 g of butanediol diglycidyl ether, 7.5 g of dodecenylsuccinic anhydride, 6 g of an oligomeric fatty acid mixture obtained by dimerisation of unsaturated higher fatty acids and having an acid equivalent weight of 292 and 1 g of a solution of 0.82 g of sodium in 100 g of 2,4-dihydroxy-3-hydroxy-methylpentane as the catalyst, with the addition of 400 g of quartz powder as a filler, at 120°C, and the mixture is poured into an aluminium mould warmed to 120°C and is cured at this temperature for 10 hours.

The mouldings obtained have the following properties: $H_2O$ absorption

| | | |
|---|---|---|
| at 23°C after | 20 days | 0.4% |
| at 23°C after | 100 days | 0.8% |
| at 100°C after | 200 hours | 1.7% |
| at 100°C after | 1,000 hours | 4.6% |
| Resistance to boiling water | | 1,600–1,800 hours |
| Dielectric loss factor (tg δ) at 120°C | | 10% |
| Tracking resistance (DIN 53,480) | | >3,000 drops |
| Surface resistance (DIN 53,482) | | $9 \times 10^{14} \Omega$ |
| $H_2O$ vapour permeability by the Deeg and Frosch method at 23°C | | $2.1 \times 10^{-8}$ |

-continued

Arcing resistance (ASTM 495)     level 3

What we claim is:

1. A polysiloxane of formula I $$HO-R_3-O-\underset{\underset{R_2}{|}}{\overset{\overset{R_1}{|}}{Si}}-\left[O-\underset{\underset{R_2}{|}}{\overset{\overset{R_1}{|}}{Si}}\right]_n-O-R_3-OH \qquad I.$$

wherein $R_1$ and $R_2$ each denote a methyl, ethyl, propyl or phenyl and $R_1$ and $R_2$ on the same Si atom denote identical substituents and within the siloxane chain denote different substituents, $R_3$ denotes an alkylene with 2–6 C atoms, a lower alkyl-substituted alkylene with 2–6 C atoms in the alkylene chain or a cycloaliphatic-aliphatic residue and $n$ denotes a number from 2 to 20.

2. A polysiloxane according to claim 1 which is a polymethylphenylsiloxanesdiol or a polypropylphenylsiloxanediol, wherein $R_3$ denotes a lower alkyl-substituted alkylene with 3 C atoms in the alkylene chain, obtained by removing a primary and a secondary hydroxyl group.

3. A polysiloxane according to claim 1 which is a polymethylphenylsiloxanediol, wherein $R_3$ denotes the 1-propyl-2-ethylpropylene or 1-propyl-2,2-dimethylpropylene residue.

4. A polysiloxane according to claim 1 wherein $R_1$ and $R_2$ are each methyl on one silicon atom and are each phenyl on the alternate silicon atom in the polysiloxane chain, $R_3$ denotes 1-propyl-2-ethylpropylene, and $n$ denotes 2.

* * * * *